(12) United States Patent
Kanaya et al.

(10) Patent No.: US 10,442,747 B2
(45) Date of Patent: Oct. 15, 2019

(54) METHOD FOR PURIFYING METHACRYLIC ACID AND METHOD FOR PRODUCING METHACRYLIC ACID

(71) Applicant: Mitsubishi Chemical Corporation, Chiyoda-ku (JP)

(72) Inventors: Koji Kanaya, Chiyoda-ku (JP); Tomomichi Hino, Chiyoda-ku (JP); Shinpei Kato, Chiyoda-ku (JP); Takafumi Toyoda, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/155,027

(22) Filed: Oct. 9, 2018

(65) Prior Publication Data

US 2019/0039987 A1    Feb. 7, 2019

Related U.S. Application Data

(63) Continuation of application No. PCT/JP2017/016289, filed on Apr. 25, 2017.

(30) Foreign Application Priority Data

Apr. 28, 2016   (JP) .................. 2016-090892

(51) Int. Cl.
    *C07C 51/43*    (2006.01)
    *B01D 9/00*    (2006.01)
    *C07C 57/04*    (2006.01)

(52) U.S. Cl.
    CPC .............. *C07C 51/43* (2013.01); *B01D 9/005* (2013.01); *B01D 9/0009* (2013.01); *B01D 9/0013* (2013.01); *B01D 9/0077* (2013.01); *C07C 57/04* (2013.01); *B01D 9/0063* (2013.01); *B01D 2009/0086* (2013.01)

(58) Field of Classification Search
    CPC .............................. C07C 51/43; B01D 9/0009
    See application file for complete search history.

(56) References Cited

U.S. PATENT DOCUMENTS

| 6,380,427 B1 | 4/2002 | Miyazaki et al. |
| 2014/0364646 A1 | 12/2014 | Hino et al. |

FOREIGN PATENT DOCUMENTS

| JP | 2010-59107 | 3/2010 |
| JP | 2011-11986 | 1/2011 |
| JP | 2011-219376 | 11/2011 |
| JP | 2012-246263 | 12/2012 |
| JP | WO2013/103112 A1 | 7/2013 |
| WO | WO99/06348 | 2/1999 |

OTHER PUBLICATIONS

International Search Report dated May 30, 2017 in PCT/JP2017/016289, filed on Apr. 25, 2017.
Written Opinion dated May 30, 2017 in PCT/JP2017/016289, filed on Apr. 25, 2017.

*Primary Examiner* — Sikarl A Witherspoon
(74) *Attorney, Agent, or Firm* — Oblon, McClelland, Maier & Neustadt, L.L.P.

(57) ABSTRACT

A method for purifying methacrylic acid, including mixing raw material methacrylic acid and methanol; precipitating a crystal of methacrylic acid from the mixed solution; and separating the crystal and mother liquor, wherein the raw material methacrylic acid and methanol are mixed so that a concentration of methanol in the mixed liquid is 3.0 to 3.75% by mass, and the crystal of methacrylic acid is precipitated from the mixed solution in a cooling crystallization vessel.

14 Claims, 1 Drawing Sheet

METHOD FOR PURIFYING METHACRYLIC ACID AND METHOD FOR PRODUCING METHACRYLIC ACID

TECHNICAL FIELD

The present invention relates to a method for purifying methacrylic acid and a method for producing methacrylic acid.

BACKGROUND ART

Methods for producing methacrylic acid include a method in which isobutylene, tertiary butyl alcohol, methacrolein, or isobutyraldehyde is subjected to catalytic gas phase oxidation with molecular oxygen in a one- or two-stage reaction. In addition to methacrylic acid (boiling point 161° C./760 mmHg, melting point 15° C.), the target substance, for example, carboxylic acids such as formic acid, acetic acid, propionic acid, maleic acid, citraconic acid, benzoic acid, toluic acid, terephthalic acid, and acrylic acid, and aldehydes such as formaldehyde, acetaldehyde, propionaldehyde, methacrolein, benzaldehyde, tolualdehyde, and furfural are contained as by-products in a product obtained by this method.

Most of these impurities are separated by purification means such as an extraction operation, a distillation operation, or a combination thereof, and methacrylic acid having a certain level of purity can be obtained.

Methods for purifying methacrylic acid include a crystallization method in addition to an extraction method and a distillation method.

Patent Literature 1 describes a method in which methanol, ethanol, propanol, butanol, or the like as a second component is added to crude methacrylic acid, methacrylic acid is crystallized from this solution, and the precipitated crystals and the mother liquor are separated to obtain purified methacrylic acid.

Patent Literature 2 describes a method of performing crystallization with a solution obtained by adding methanol as a second component to crude methacrylic acid, using a continuous crystallization apparatus in which a first crystallization vessel and a second crystallization vessel are connected, and in the method, methacrylic acid is crystallized in a state in which some of the suspension slurry in the second crystallization vessel is circulated to the first crystallization vessel, and crystals precipitated in a purification column and mother liquor are separated to obtain purified methacrylic acid.

Patent Literature 3 describes a method in which crystallization is performed using a scraper unit having a structure that effectively suppresses the growth of a crystal layer on a cooling surface, thereby stably obtaining purified methacrylic acid for a long period.

CITATION LIST

Patent Literature

Patent Literature 1: WO 99/06348
Patent Literature 2: JP2011-219376A
Patent Literature 3: JP2012-246263A

SUMMARY OF INVENTION

Technical Problem

Since aldehydes contained in methacrylic acid as impurities has absorption in the ultraviolet region, there is a problem that coloration occurs in methacrylic acid products in which large amounts of aldehydes remain. By a usual extraction method and distillation method, it has been difficult to sufficiently remove aldehydes, and it has been difficult to solve such a problem of coloration.

As means for removing impurities difficult to decrease by distillation, the crystallization method described in Patent Literature 1 is proposed. But, in this method, the concentration range of the second component added to the crude methacrylic acid is very wide, 1 to 35% by mass or 3 to 30% by mass, and operating conditions under which purification can be more efficiently performed than under the described operating conditions are not clearly shown.

In addition, the second component added to the crude methacrylic acid needs to be finally removed like other impurities. Therefore, the second component content in the crystal group subjected to solid-liquid separation after the crystallization operation is preferably low, but a method for efficiently achieving this is also not shown.

For the method described in Patent Literature 2, it is shown that by circulating the suspension slurry in the second crystallization vessel to the first crystallization vessel, the equalization of the cooling loads on both vessels is promoted, and scaling in the first crystallization vessel is suppressed, and thus running for a long period can be achieved, but the quality of methacrylic acid is not shown.

For the method described in Patent Literature 3, it is shown that running for a long period can be achieved using the scraper unit, but the quality and productivity of methacrylic acid are not shown.

The present invention has been made in view of the above circumstances, and it is an object of the present invention to provide a method for purifying methacrylic acid and a method for producing methacrylic acid that can increase the purity of a crystal group after solid-liquid separation and can attain high productivity.

Solution to Problem

According to one aspect of the present invention, there is provided
a method for purifying methacrylic acid, including:
mixing raw material methacrylic acid and methanol;
precipitating a crystal of methacrylic acid from a mixed solution containing the raw material methacrylic acid and methanol; and
separating the crystal and mother liquor,
wherein methanol is mixed so that a concentration of methanol in the mixed solution is 3.0 to 3.75% by mass, and the crystal of methacrylic acid is precipitated from the mixed solution in a cooling crystallization vessel.

According to another aspect of the present invention, there is provided
a method for producing methacrylic acid, including the steps of:
forming raw material methacrylic acid; and
purifying the raw material methacrylic acid by the above method for purifying.

According to another aspect of the present invention, there is provided
a method for producing methacrylic acid, including the steps of:
forming raw material methacrylic acid;
purifying the raw material methacrylic acid by the above purification method; and subjecting, to solid-liquid separation, a suspension slurry formed in the above step of purifying, and purifying an obtained solid by a high purity operation.

Advantageous Effect of Invention

According to the present invention, it is possible to provide a method for purifying methacrylic acid and a method for producing methacrylic acid that can increase the purity of a crystal group after solid-liquid separation and can attain high productivity.

DESCRIPTION OF EMBODIMENTS

Figure 1:
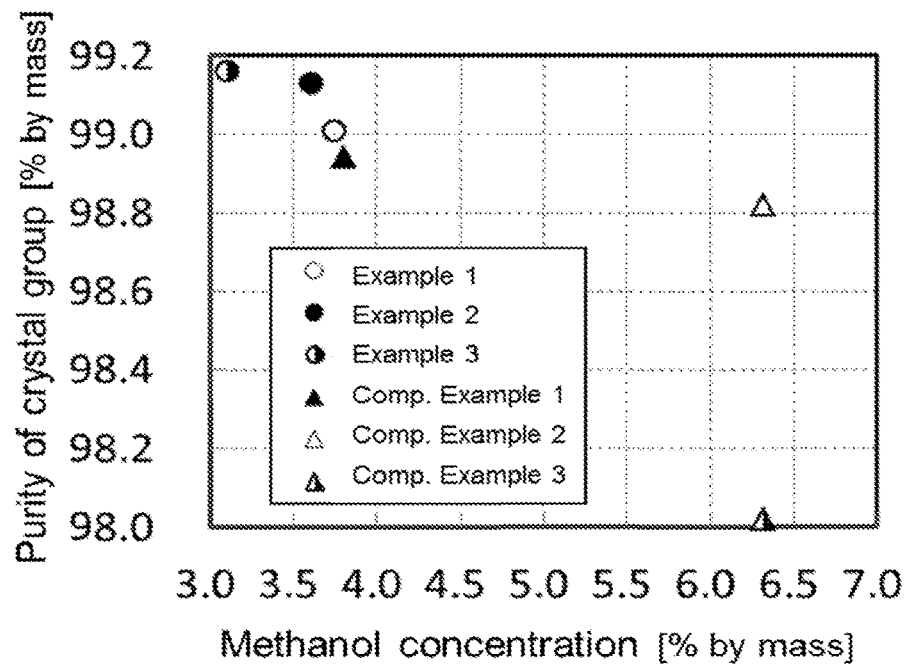
FIG. 1 is a graph showing the relationship between methanol concentration and the purity of crystal groups.

The present inventors have studied diligently and as a result found that by setting the solvent concentration in a raw material and the temperature in a crystallization vessel within particular ranges, the crystal precipitation rate can be increased while high crystal group purity after solid-liquid separation is maintained, and further by using a particular crystallization apparatus, the crystal precipitation rate can be further increased while high crystal group purity after solid-liquid separation is maintained, leading to the completion of the present invention. The temperature in a crystallization vessel indicates the temperature of a suspension slurry in the crystallization vessel. The crystal precipitation rate is the amount of crystals produced per unit time.

A method according to an embodiment of the present invention is a method for purifying methacrylic acid, including mixing raw material methacrylic acid and methanol; precipitating crystals of methacrylic acid from the mixed solution containing the above raw material methacrylic acid and methanol; and separating the above crystals and the mother liquor, wherein methanol is mixed so that the concentration of methanol in the above mixed solution is 3.0 to 3.75% by mass, and the crystals of methacrylic acid are precipitated from the above mixed solution in a cooling crystallization vessel.

In the above purification method, the temperature in the above cooling crystallization vessel is preferably controlled in the range of 4 to 8° C. By controlling the temperature in the crystallization vessel in this temperature range, the crystals can be sufficiently precipitated.

In the above purification method, preferably, the above raw material methacrylic acid and methanol are mixed so that the concentration of methanol in the above mixed solution is 3.0 to 3.75% by mass, and then the mixed solution is supplied to the above cooling crystallization vessel. For example, it is possible to previously mix the raw material methacrylic acid and methanol to prepare the above mixed solution in which the concentration of methanol is 3.0 to 3.75% by mass, and supply this mixed solution to the above cooling crystallization vessel.

In the above purification method, the above mixed solution is preferably continuously supplied to the above cooling crystallization vessel. On the other hand, the slurry containing the precipitated crystals and the mother liquor is preferably continuously or intermittently drawn from this cooling crystallization vessel. At this time, the slurry is preferably drawn so that the position of the liquid surface in the cooling crystallization vessel is substantially constant.

In the above purification method, the above mixed solution at 9 to 20° C. is preferably supplied to the above cooling crystallization vessel. When the temperature of the above mixed solution is higher than 20° C., the mixed solution is preferably supplied after the mixed solution is cooled to the range of 9 to 20° C.

In the above purification method, preferably, the cooling crystallization vessel is equipped with a baffle-equipped cylindrical container equipped with a cooling jacket, and includes, inside the cylindrical container, a scraper unit for scraping crystals precipitated on the inner surface of the cylindrical container, a rotating shaft, and an anchor-shaped scraper arm linking the rotating shaft and the scraper unit.

The above scraper unit is preferably equipped with a scraper blade for scraping crystals precipitated on the inner surface of the above cylindrical container; a scraper blade holder having a blade supporting portion supporting the scraper blade, and an arm coupling portion fixed to the above scraper arm; and a spring type pressing apparatus for pressing the scraper blade against the inner surface of the cylindrical container via the blade supporting portion. Preferably, the above blade supporting portion and the above arm coupling portion are movably connected, the blade supporting portion and the above spring type pressing apparatus are movably connected, and the spring type pressing apparatus and the above scraper arm are movably connected.

Further, preferably, the lower portion of the above scraper arm is a flat paddle blade portion, and the flat paddle blade includes a portion in which the length of the flat paddle blade portion in the axial direction of the above cylindrical container shortens gradually from the above rotating shaft toward the direction of the side surface of the above cylindrical container.

The purification method according to the embodiment of the present invention can be preferably carried out, for example, using the crystallization apparatus described in JP5708257B (JP2012-246263A). As this crystallization apparatus, the following crystallization apparatus can be used.

A crystallization apparatus that can be preferably used in the purification method according to the embodiment of the present invention is a crystallization apparatus for crystallizing methacrylic acid from a raw material containing methacrylic acid by indirect cooling crystallization to obtain a crystal slurry, the crystallization apparatus being an apparatus for crystallizing methacrylic acid, equipped with a baffle-equipped cylindrical container equipped with a cooling jacket, as a crystallization vessel, a motor-driven rotating shaft passing through the cylindrical container in the axial direction of the cylindrical container, and a bearing supporting the rotating shaft and disposed on the bottom surface of the cylindrical container, and the crystallization apparatus including, inside the cylindrical container, a scraper unit for scraping crystals precipitated on the inner surface of the cylindrical container, an anchor-shaped scraper arm linking the rotating shaft and the scraper unit, and a ring support attached to the scraper arm and reinforcing the scraper arm.

In the above crystallization apparatus, the above scraper unit is a scraper unit for an apparatus for crystallizing methacrylic acid, the scraper unit being used by being attached to a scraper arm, and equipped with a scraper blade for scraping crystals precipitated on the inner surface of a crystallization vessel, a scraper blade holder having a blade supporting portion supporting the scraper blade, and an arm coupling portion fixed to the scraper arm, and a spring type pressing apparatus for pressing the scraper blade against the inner surface of the crystallization vessel via the blade supporting portion, wherein the blade supporting portion and the arm coupling portion are movably connected, the blade supporting portion and the spring type pressing apparatus are movably connected, and the spring type pressing apparatus and the scraper arm are movably connected.

In the above crystallization apparatus, preferably, the lower portion of the above anchor-shaped scraper arm is a flat paddle blade portion, and the length of the flat paddle blade portion in the axial direction of the above cylindrical container shortens gradually from the above rotating shaft toward the direction of the side surface of the above cylindrical container.

Preferably, the above crystallization apparatus is used, and the power required for stirring per unit volume in the above crystallization vessel is 0.15 kW/m$^3$ or more and 0.7 kW/m$^3$ or less.

As specific structures of such a crystallization apparatus, the structures shown in FIG. 1, FIG. 2, FIG. 3, and FIG. 4, and the description of these figures in JP5708257B (JP2012-246263A) can be adopted.

In the above purification method, preferably, the obtained suspension slurry is further subjected to solid-liquid separation, and a high purity operation is performed.

The details of the purification method according to the embodiment of the present invention will be shown below, but the present invention is not limited to these.

In the embodiment of the present invention, as the raw material for producing the crystals, crude methacrylic acid or methacrylic acid obtained by purifying crude methacrylic acid by a method such as precision distillation or crystallization can be used. The raw material methacrylic acid is methacrylic acid containing impurities to be removed by the purification method according to the present invention, and even methacrylic acid purified by another purification method such as distillation or crystallization is included in the raw material methacrylic acid to be purified by the method of the present invention if it contains impurities to be removed by the method of the present invention. Crude methacrylic acid and methacrylic acid obtained by purifying crude methacrylic acid will be hereinafter described as "raw material methacrylic acid" as the raw material for purification according to the present invention.

Raw material methacrylic acid can be produced by various methods, for example, a direct oxidation method and an ACH (acetone cyanohydrin) method.

Examples of such methods for producing raw material methacrylic acid include a method in which from a condensate obtained by condensing a reaction gas obtained by a direct oxidation method in which at least one compound selected from the group consisting of isobutylene, tertiary butyl alcohol, methacrolein, and isobutyraldehyde is subjected to catalytic gas phase oxidation with molecular oxygen in a one- or two-stage reaction, or from a methacrylic acid aqueous solution obtained by adding water to a condensate of the reaction gas or absorbing the reaction gas by water, methacrylic acid is extracted using an organic solvent, and the organic solvent and nonvolatile matter are removed by distillation to obtain raw material methacrylic acid. At this time, as the organic solvent, n-heptane, dimethylcyclohexane, ethylcyclohexane, toluene, ethylbenzene, chlorobenzene, xylene, diethyl ketone, diisopropyl ketone, methyl propyl ketone, methyl isobutyl ketone, methyl-t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valerate, ethyl butyrate, dibutyl ether, and mixtures thereof, and a solvent containing at least one selected from them can be used. In addition, examples of the methods for producing raw material methacrylic acid include a method in which methacrylic acid produced as a by-product by an ACH method is separated by extraction or distillation to obtain raw material methacrylic acid. The purity of the raw material methacrylic acid is preferably 99.00% by mass or more, more preferably 99.00 to 99.99% by mass, and further preferably 99.00 to 99.90% by mass.

In the purification method according to the embodiment of the present invention, a mixed solution obtained by adding a solvent to raw material methacrylic acid can be used as the crystallization raw material. As this solvent, polar substances such as methanol, ethanol, propanol, and water can be used, but methanol is preferably used in terms of the improvement of the fluidity of the suspension slurry, and the suppression of scaling on the cooling transfer surface.

The method for supplying the raw material methacrylic acid and methanol to the crystallization vessel is not particularly limited. Examples thereof include a method of continuously or intermittently supplying predetermined amount of each of the raw material methacrylic acid and methanol to the crystallization vessel. A case where the raw material methacrylic acid and methanol are each continuously supplied is preferred because the methanol concentration in the crystallization vessel can be controlled to be constant by making each mass flow rate constant.

On the other hand, when methanol is intermittently supplied, it is necessary to sample the slurry in the crystallization vessel and analyze the concentration of methanol, the solvent, which requires effort. Therefore, a predetermined amount of methanol is preferably continuously supplied as described above, and methanol is more preferably continuously supplied as described below.

In other words, preferably, the raw material methacrylic acid and methanol are mixed so that methanol is at a predetermined concentration, and then the mixed liquid is continuously supplied to the crystallization vessel. For example, it is possible to previously make a mixed solution of the raw material methacrylic acid and methanol so that methanol is at a predetermined concentration, and continuously supply this mixed solution to the crystallization vessel.

It is possible to prepare the mixed solution of the raw material methacrylic acid and methanol using a container such as a tank, or it is possible to mix the raw material methacrylic acid and methanol in piping while measuring each mass flow rate, and supply the mixture to the crystallization vessel as it is. The mass flow rate may be measured by a mass flowmeter, or obtained by measuring the volume flow rate, and converting the volume flow rate into the mass flow rate using the specific gravity of the liquid.

The methanol concentration in the mixed solution of the raw material methacrylic acid and methanol is preferably 3.0 to 3.75% by mass.

The methanol concentration of this mixed solution is defined by formula (1).

methanol concentration [% by mass]=(mass of methanol added as solvent)/(mass of raw material methacrylic acid+mass of methanol added as solvent)×100     (1)

When the methanol concentration of this mixed solution is 3.0% by mass or more, not only does the particle diameter of the methacrylic acid crystals in the suspension slurry decrease to improve the fluidity of the suspension slurry and solve troubles such as clogging in drawing piping and the like and crystal accumulation in the crystallization vessel, but the adhesion of the crystals to the cooling transfer surface decreases to suppress scaling. From this viewpoint, the methanol concentration of this mixed solution is 3.0% by mass or more, more preferably 3.2% by mass or more, and further preferably 3.5% by mass or more.

On the other hand, when the methanol concentration of this mixed solution is 3.75% by mass or less, the purity of the crystal group after the suspension slurry is subjected to solid-liquid separation can be maintained high. Concerning this, it is considered that when a concentration exceeding 3.75% by mass is set, the methacrylic acid crystals in the suspension slurry become smaller than necessary; and as a result, since the specific surface area increases, the amount of the mother liquor adhering to the crystal surfaces increases, and in addition, the methanol concentration in the mother liquor is high, and therefore the amount of methanol adhering to the crystal surfaces also increases. Therefore, it is desired that the methanol concentration of the mixed liquid is set not to exceed 3.75% by mass, thereby not making the crystal size smaller than necessary. From this viewpoint, the methanol concentration of this mixed liquid is preferably 3.75% by mass or less, more preferably 3.74% by mass or less, and further preferably 3.70% by mass or less. When methanol is previously present in the raw material methacrylic acid, the methanol in the raw material methacrylic acid can also be considered as methanol added as the solvent.

In the purification method according to the embodiment of the present invention, a crystallization operation for the raw material methacrylic acid is performed using the cooling crystallization vessel. As the cooling crystallization vessel, a cooler having, in a vessel, a cooling coil in which a cooling heat medium is circulated, or a cooler having, on the peripheral surface of a vessel, a cooling jacket for bringing a cooling heat medium into contact from the outside, or one equipped with both can be used. Among these, one that can cool the interior of a crystallization vessel by heat exchange using the peripheral surface of the crystallization vessel as a heat transfer surface is preferred. The cooling crystallization vessel may be arranged to have both a cooling coil and a cooling jacket.

In the purification method according to the embodiment of the present invention, the crystallization operation is preferably continuous in that the states in the vessel such as temperature in crystallization vessel, suspension density, and mother liquor composition that influence productivity and the quality of the crystals are kept constant. The suspension density is the mass concentration of the crystals in the suspension slurry in the crystallization vessel.

The temperature in the cooling crystallization vessel is preferably 4 to 8° C. By setting the temperature in the cooling crystallization vessel at 4° C. or more, the above-described effects such as the improvement of the fluidity of the suspension slurry and the suppression of scaling can be sufficiently obtained. In this regard, the temperature in the cooling crystallization vessel is preferably 4° C. or more, more preferably 5° C. or more. Further, according to the study of the present inventors, it has become clear that the lower the temperature in the crystallization vessel is, the more the purity of the crystal group obtained by subjecting the suspension slurry to solid-liquid separation decreases. Also in this regard, it is important to keep the temperature in the crystallization vessel at this temperature or more. On the other hand, when the temperature in the crystallization vessel exceeds 8° C., the suspension slurry concentration decreases significantly, causing a large decrease in productivity, which is not preferred. From this viewpoint, the temperature in the cooling crystallization vessel is preferably 8° C. or less, more preferably 7° C. or less, and further preferably 6° C. or less.

When the temperature of the mixed solution of the raw material methacrylic acid and methanol is higher than 20° C. when this mixed solution is supplied to the above cooling crystallization vessel, this mixed solution is preferably cooled to the range of 9 to 20° C. (more preferably the range of 9 to 15° C.) and then supplied to the above cooling crystallization vessel. Thus, the cooling load in the crystallization vessel can be decreased.

The freezing point of the raw material methacrylic acid depends on its purity but is around 15° C. at atmospheric pressure. Therefore, when only the raw material methacrylic acid is supplied to the crystallization vessel, it is necessary to set the temperature of the raw material methacrylic acid at a temperature higher than the freezing point, that is, a temperature higher than 15° C., when cooling the raw material methacrylic acid before the supply. In this temperature range, it is difficult to obtain a large effect of decreasing the cooling load in the crystallization vessel. In such a case, the raw material methacrylic acid and methanol are preferably previously mixed to form a mixed solvent. Thus, the freezing point of the mixed solvent can be lowered, and the cooling load in the crystallization vessel can be sufficiently decreased.

The cooling crystallization vessel is preferably equipped with a baffle-equipped cylindrical container equipped with a cooling jacket, and includes, inside the cylindrical container, a scraper unit for scraping crystals precipitated on the inner surface of the cylindrical container, a rotating shaft, and an anchor-shaped scraper arm linking the rotating shaft and the scraper unit.

By equipping the crystallization vessel (cylindrical container) with a baffle, the settling of crystals on the crystallization vessel bottom can be suppressed. In addition, the raw material concentration distribution and the temperature distribution in the vessel can be made uniform, and a local increase in the degree of supersaturation can be suppressed.

The above scraper unit is preferably equipped with a scraper blade for scraping crystals precipitated on the inner surface of the above cylindrical container; a scraper blade holder having a blade supporting portion supporting the scraper blade, and an arm coupling portion fixed to the above scraper arm; and a spring type pressing apparatus for pressing the scraper blade against the inner surface of the cylindrical container via the blade supporting portion.

By using the scraper unit, scraping can be uniformly performed without the rotating shaft swinging even when running with relatively high rotation also aimed at mixing and stirring in the crystallization vessel is performed.

Further, preferably, the lower portion of the above scraper arm is a flat paddle blade portion, and has a portion in which the length of the flat paddle blade portion in the axial direction of the above cylindrical container shortens gradually from the above rotating shaft toward the direction of the side surface of the above cylindrical container.

By using the flat paddle blade portion, not only can a flow of crystals settled on the bottom of the crystallization vessel (cylinder container) swirling up to the upper portion be formed to easily perform good mixing in the vessel, but poor drawing at the discharge nozzle can be easily suppressed.

The suspension slurry obtained in the cooling crystallization vessel is drawn from the crystallization vessel and then subjected to solid-liquid separation. The method of solid-liquid separation is not particularly limited, and, for example, known solid-liquid separation apparatuses such as a filtration apparatus and a centrifugal apparatus, and combinations thereof can be used. The mother liquor containing impurities, and methanol remain in the crystal group that is solids obtained after the solid-liquid separation. In order to separate and remove the mother liquor and methanol, a high purity operation can be performed. As the operation of making the purity of the obtained crystal group even higher, purification including the operation of making the purity higher in the crystal state can be performed, and specifically, purification including the operation of raising the crystal temperature to release the impurities (for example, the mother liquor and methanol) in the crystals out of the crystals, using a phenomenon referred to as the "sweating" of crystals can be performed. Specific examples of the apparatus for performing such a high purity operation include KCP (Kureha Crystal Purifier) that is a continuous crystal purification apparatus manufactured by Kureha Ecology Management Co., Ltd., appearing in Chuzo Shimizu, "Kureha Renzokukesshoseiseisochi Niyoru Yukikagobutsu No Seisei (Purification of Organic Compounds by Kureha Continuous Crystal Purification Apparatus)", CHEMICAL ENGINEERING, Vol. 27, No. 3, (1982), p. 49. The operation of separation can be conducted by either a batch operation or a continuous operation.

EXAMPLES

The present invention will be specifically described below by giving Examples, but the present invention is not limited to these Examples.

In the Examples and Comparative Examples, a crystallization operation was performed using, as the crystallization apparatus, a continuous jacket-cooling crystallization vessel (volume 5 L) made of stainless steel equipped with a stirring mechanism with a flat paddle blade, a scraper unit, and a baffle. As the heat medium, a 40% by mass ethylene glycol aqueous solution was used.

For component concentration measurement, gas chromatography (main body: GC-17A (product name), manufactured by SHIMADZU CORPORATION, analytical column: HP-FFAP (trade name), manufactured by Agilent Technologies) was used.

Example 1

Tertiary butyl alcohol was subjected to catalytic gas phase oxidation with molecular oxygen, the obtained reaction gas was absorbed by water, methacrylic acid was extracted from the obtained methacrylic acid aqueous solution using n-heptane, and this extract was distilled to remove the organic solvent and nonvolatile matter to obtain crude methacrylic acid. This crude methacrylic acid was subjected to purification by a crystallization operation to obtain purified methacrylic acid (purity: 99.98% by mass). In this Example, this purified methacrylic acid was used as raw material methacrylic acid.

Methanol at 25° C. as a solvent was mixed with the above raw material methacrylic acid maintained at 22° C. so that the concentration was 3.74% by mass, thereby preparing a mixed solution of the raw material methacrylic acid and methanol.

This mixed solution was cooled to 10° C., then the crystallization vessel was charged with 3.4 L of the mixed solution, and the heat medium at 10° C. was supplied to the jacket of the crystallization vessel under the stirring condition of 125 rpm.

Then, the heat medium temperature was lowered at 2.0° C./hr. At the point in time when the heat medium temperature reached 4.5° C., the supply of the above mixed solution cooled to 10° C. to the crystallization vessel was started at a flow rate of 1.1 kg/hr, and the slurry in the vessel was intermittently drawn so that the position of the liquid surface in the crystallization vessel was constant.

The drawn slurry was transferred to a glass column (inner diameter: 70 mm, height: 400 mm) in which a filter was mounted in the lower portion, and gravity-filtered. The composition of the obtained mother liquor and the temperature in the crystallization vessel were confirmed.

Figure 2:
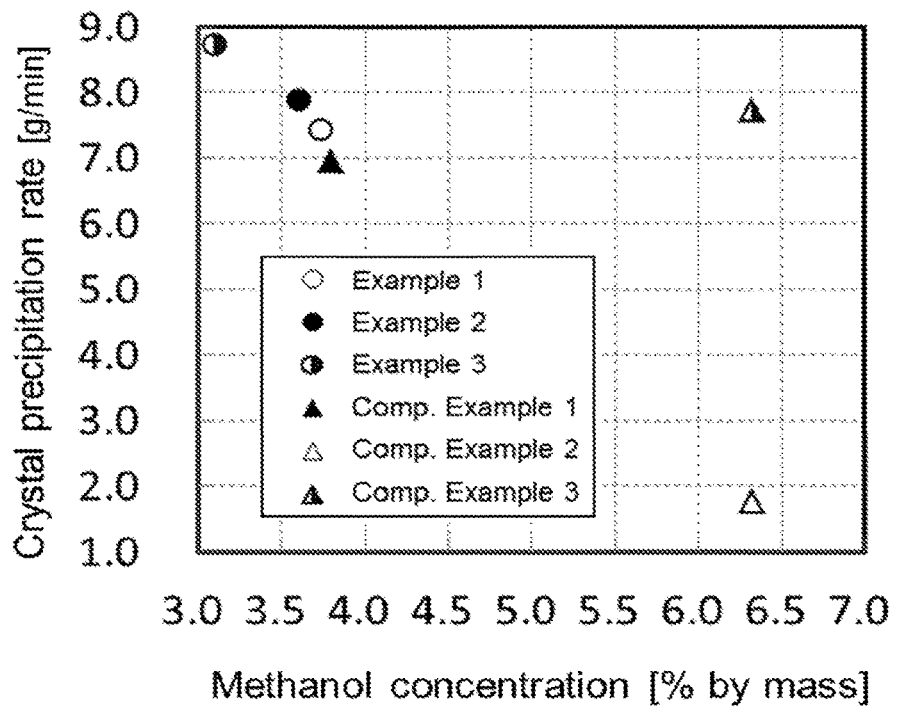
FIG. 2 is a graph showing the relationship between methanol concentration and crystal precipitation rate.

This continuous running operation was continued for 4 hours, and from changes in the composition of the obtained mother liquor and the temperature in the crystallization vessel over time, it was confirmed that a steady state was reached in the vessel. The purity of the obtained crystal group and the temperature in the crystallization vessel, the suspension density, and the crystal precipitation rate in the steady state are shown in Table 1. The relationship between the methanol concentration and the purity of the crystal group, and the relationship between the methanol concentration and the crystal precipitation rate are shown in FIG. 1 and FIG. 2 respectively.

Then, the obtained crystal group was subjected to a high purity operation so that the methacrylic acid purity was 99.98% by mass or more. For the high purity operation, KCP (Kureha Crystal Purifier) that was a continuous crystal purification apparatus manufactured by Kureha Ecology Management Co., Ltd. was used. The productivity ratio of the obtained methacrylic acid is shown in Table 2.

The purity of the crystal group shown in the Examples and the Comparative Examples was calculated with methanol contained in the crystal group also considered as an impurity.

For the suspension density, the total mass of the sampled slurry was measured, then the slurry was subjected to solid-liquid separation by a method such as filtration, the mass of the crystals was measured, and then the suspension density was calculated by the following formula (1).

$$\text{suspension density [\% by mass]} = \text{mass of crystals [kg]/mass of slurry [kg]} \times 100 \quad (1)$$

The crystal precipitation rate was calculated by the following formula (2).

$$\text{crystal precipitation rate [g/min]} = (\text{raw material supply rate or slurry drawing rate [g/min]}) \times (\text{suspension density difference between raw material and drawn slurry [\% by mass]})/100 \quad (2)$$

The productivity ratio was calculated by the following formula (4) based on the value of productivity represented by the following formula (3) and based on the value in Comparative Example 1.

productivity=amount of purified methacrylic acid [kg] obtained by high purity operation    (3)

productivity ratio=productivity in each Example or Comparative Example/productivity in Comparative Example 1    (4)

Example 2

The purification operation was performed as in Example 1 except that the methanol concentration in the mixed solution of the raw material methacrylic acid and methanol was 3.60% by mass. The purity of the crystal group, the temperature in the crystallization vessel, the suspension density, and the crystal precipitation rate were measured as in Example 1. The results are shown in Table 1. The relationship between the methanol concentration and the purity of the crystal group, and the relationship between the methanol concentration and the crystal precipitation rate are shown in FIG. 1 and FIG. 2 respectively.

Then, the obtained crystal group was subjected to the high purity operation as in Example 1. The productivity ratio of the obtained methacrylic acid is shown in Table 2.

Example 3

The purification operation was performed as in Example 1 except that the methanol concentration in the mixed solution of the raw material methacrylic acid and methanol was 3.10% by mass. The purity of the crystal group, the temperature in the crystallization vessel, the suspension density, and the crystal precipitation rate were measured as in Example 1. The results are shown in Table 1. The relationship between the methanol concentration and the purity of the crystal group, and the relationship between the methanol concentration and the crystal precipitation rate are shown in FIG. 1 and FIG. 2 respectively.

Then, the obtained crystal group was subjected to the high purity operation as in Example 1. The productivity ratio of the obtained methacrylic acid is shown in Table 2.

Comparative Example 1

The purification operation was performed, and the purity of the crystal group, the temperature in the crystallization vessel, the suspension density, and the crystal precipitation rate were measured, as in Example 1 except that the methanol concentration in the mixed solution of the raw material methacrylic acid and methanol was 3.80% by mass. The results are shown in Table 1. The relationship between the methanol concentration and the purity of the crystal group, and the relationship between the methanol concentration and the crystal precipitation rate are shown in FIG. 1 and FIG. 2 respectively.

Then, the obtained crystal group was subjected to the high purity operation as in Example 1. The productivity ratio of the obtained methacrylic acid is shown in Table 2.

Comparative Example 2

The purification operation was performed, and the purity of the crystal group, the temperature in the crystallization vessel, the suspension density, and the crystal precipitation rate were measured, as in Example 1 except that the methanol concentration in the mixed solution of the raw material methacrylic acid and methanol was 6.32% by mass, and the crystallization raw material (the above mixed liquid) was supplied to the crystallization vessel at 1.4 kg/hr. The results are shown in Table 1. The relationship between the methanol concentration and the purity of the crystal group, and the relationship between the methanol concentration and the crystal precipitation rate are shown in FIG. 1 and FIG. 2 respectively.

Then, the obtained crystal group was subjected to the high purity operation as in Example 1. The productivity ratio of the obtained methacrylic acid is shown in Table 2.

Comparative Example 3

The purification operation was performed, and the purity of the crystal group, the temperature in the crystallization vessel, the suspension density, and the crystal precipitation rate were measured, as in Comparative Example 2 except that at the point in time when the heat medium temperature reached 1.5° C., the crystallization raw material (the above mixed liquid) was supplied to the crystallization vessel. The results are shown in Table 1. The relationship between the methanol concentration and the purity of the crystal group, and the relationship between the methanol concentration and the crystal precipitation rate are shown in FIG. 1 and FIG. 2 respectively.

Then, the obtained crystal group was subjected to the high purity operation as in Example 1. The productivity ratio of the obtained methacrylic acid is shown in Table 2.

Comparative Example 4

The same operation as Example 1 was performed except that the methanol concentration in the mixture of the raw material methacrylic acid and methanol was 2.90% by mass. However, 2 hours after the start of the supply of the crystallization raw material (the above mixed liquid), the flowing state of the suspension slurry deteriorated, and the clogging of the drawing piping occurred, and a scale formed on the cooling transfer surface, and therefore the running was stopped.

Comparative Example 5

The purification operation was performed as in Example 1, with the methanol concentration in the mixed solution of the raw material methacrylic acid and methanol being 3.80% by mass, using an apparatus equipped with only a stirring mechanism for the crystallization apparatus. The purity of the crystal group, the temperature in the crystallization vessel, the suspension density, and the crystal precipitation rate were measured as in Example 1. The results are shown in Table 1. The relationship between the methanol concentration and the purity of the crystal group, and the relationship between the methanol concentration and the crystal precipitation rate are shown in FIG. 1 and FIG. 2 respectively.

Then, the obtained crystal group was subjected to the high purity operation as in Example 1. The productivity ratio of the obtained methacrylic acid is shown in Table 2.

TABLE 1

| | Methanol concentration [% by mass] | Temperature in vessel [° C.] | Purity of crystal group [% by mass] | Suspension density [% by mass] | Crystal precipitation rate [g/min] |
|---|---|---|---|---|---|
| Example 1 | 3.74 | 5.34 | 99.01 | 40.53 | 7.43 |
| Example 2 | 3.60 | 5.36 | 99.13 | 43.04 | 7.89 |
| Example 3 | 3.10 | 5.60 | 99.16 | 46.42 | 8.51 |
| Comparative Example 1 | 3.80 | 5.32 | 98.94 | 37.80 | 6.93 |
| Comparative Example 2 | 6.32 | 5.18 | 98.82 | 7.55 | 1.76 |
| Comparative Example 3 | 6.32 | 2.36 | 98.02 | 33.04 | 7.71 |
| Comparative Example 4 | 2.90 | — | — | — | — |
| Comparative Example 5 | 3.80 | 5.55 | 98.92 | 33.80 | 6.20 |

TABLE 2

| | Productivity ratio |
|---|---|
| Example 1 | 1.10 |
| Example 2 | 1.17 |
| Example 3 | 1.26 |
| Comparative Example 1 | 1.00 |
| Comparative Example 2 | 0.26 |
| Comparative Example 3 | 1.05 |
| Comparative Example 4 | — |
| Comparative Example 5 | 0.89 |

In Examples 1, 2, and 3 in which the methanol concentration was 3.74% by mass, 3.60% by mass, and 3.10% by mass, the crystal precipitation rate improved by 7%, 14%, and 23% respectively with respect to Comparative Example 1 in which the methanol concentration was 3.8% by mass. In addition, the purity of the crystal group after solid-liquid separation in Examples 1, 2, and 3 improved by 0.07 points, 0.19 points, and 0.22 points respectively with respect to the purity in Comparative Example 1. Further, the productivity ratios in Examples 1, 2, and 3 improved to 1.10, 1.17, and 1.26 respectively with respect to Comparative Example 1 (1.0).

On the other hand, in Comparative Example 2 in which the methanol concentration was increased to 6.32% by mass, not only did the crystal precipitation rate decreased significantly, but the purity of the crystal group after solid-liquid separation also decreased, and as a result, the productivity ratio also deteriorated significantly. In addition, in Comparative Example 3 in which the methanol concentration was increased to 6.32% by mass, and, the temperature in the crystallization vessel was lowered to about 2° C., the improvement of the crystal precipitation rate at the same level as Example 1 was seen, but the purity of the crystal group after solid-liquid separation decreased by about 1 point compared with Examples 1, 2, and 3. The productivity ratio improved slightly but fell short of the results in Examples 1, 2, and 3.

In addition, in Comparative Example 4 in which the methanol concentration was as low as 2.9% by mass, not only did the fluidity of the suspension slurry deteriorate, but a scale formed on the cooling transfer surface, and stable running was impossible.

In addition, in Comparative Example 5 in which the purification operation was performed by the crystallization apparatus equipped with only the stirring mechanism, with the methanol concentration being 3.8% by mass, the same as Comparative Example 1, scaling on the cooling transfer surface in the vessel proceeded, and the heat removal ability decreased, and therefore the productivity ratio fell short of the result in Comparative Example 1.

From the above results, according to the purification method according to the embodiment of the present invention, it is possible to improve the crystal precipitation rate directly linked with productivity, and the purity of the crystal group after solid-liquid separation and as a result also increase productivity.

In addition, in the present Examples and the Comparative Examples, the purified methacrylic acid (purity: 99.98% by mass) subjected to crystallization is used as the raw material methacrylic acid, and therefore the main impurity component is methanol, and from the above result, it is seen that the amount of methanol mixed with the raw material methacrylic acid that remains in the crystals can be decreased.

In the purification method according to the embodiment of the present invention, crude methacrylic acid can be used as the raw material methacrylic acid as described above, and the content of the impurities in this crude methacrylic acid can be decreased by the purification method according to this embodiment.

The fact that impurities can be decreased by the above purification method when crude methacrylic acid is used for raw material methacrylic acid will be specifically described by giving a Reference Example.

Reference Example 1

The purification operation was performed as in Example 1 except that crude methacrylic acid was used for the raw material methacrylic acid. The concentrations of the impurities in the crystal group excluding methanol were measured.

For the component concentration measurement, gas chromatography (main body: GC-2014AFsc (product name), manufactured by SHIMADZU CORPORATION, analytical column: DP-FFAP (trade name), manufactured by Agilent Technologies) was used.

The impurity concentrations in the raw material methacrylic acid, and the concentrations of the impurities in the crystal group obtained in Reference Example 1 are shown in Table 3.

TABLE 3

| Impurities | Impurity concentrations in raw material methacrylic acid (ppm by mass) | Impurity concentrations of crystal group (Reference Example 1) (ppm by mass) |
|---|---|---|
| Acetic acid | 25 | 9 |
| Propionic acid | 263 | 116 |
| Acrylic acid | 1300 | 664 |
| Tolualdehyde | 366 | 137 |
| Phenol | 138 | 50 |

By using crude methacrylic acid as raw material methacrylic acid, and performing the crystallization operation shown in the present Examples using a mixed liquid of this crude methacrylic acid and methanol, a crystal group in which the impurities in the raw material are decreased can be obtained.

The invention claimed is:

1. A method for purifying methacrylic acid, comprising:
mixing raw material methacrylic acid having a purity of 99.00% by mass or more and methanol;
precipitating a crystal of methacrylic acid from a mixed solution comprising the raw material methacrylic acid and methanol; and
separating the crystal and mother liquor,
wherein the raw material methacrylic acid and methanol are mixed so that a concentration of methanol in the mixed solution is 3.0 to 3.75% by mass, and
the crystal of methacrylic acid is precipitated from the mixed solution in a cooling crystallization vessel.

2. The method for purifying methacrylic acid according to claim 1, wherein a temperature in the cooling crystallization vessel is controlled in the range of 4 to 8° C.

3. The method for purifying methacrylic acid according to claim 1, wherein the raw material methacrylic acid and methanol are mixed so that the concentration of methanol in the mixed solution is 3.0 to 3.75% by mass, and then the mixed solution is supplied to the cooling crystallization vessel.

4. The method for purifying methacrylic acid according to claim 3, wherein the mixed solution is continuously supplied to the cooling crystallization vessel.

5. The method for purifying methacrylic acid according to claim 3, wherein the mixed solution having a temperature of 9 to 20° C. is supplied to the cooling crystallization vessel.

6. The method for purifying methacrylic acid according to claim 1, wherein
the cooling crystallization vessel comprises a baffle-equipped cylindrical container equipped with a cooling jacket, and
the cooling crystallization vessel comprises, inside the cylindrical container:
a scraper unit for scraping a crystal precipitated on an inner surface of the cylindrical container;
a rotating shaft; and
an anchor-shaped scraper arm linking the rotating shaft and the scraper unit.

7. The method for purifying methacrylic acid according to claim 6, wherein the scraper unit comprises:
a scraper blade for scraping a crystal precipitated on an inner surface of the cylindrical container;
a scraper blade holder comprising a blade supporting portion supporting the scraper blade, and an arm coupling portion fixed to the scraper arm; and
a spring type pressing apparatus for pressing the scraper blade against the inner surface of the cylindrical container via the blade supporting portion.

8. The method for purifying methacrylic acid according to claim 7, wherein a lower portion of the scraper arm comprises a flat paddle blade portion, and
the lower portion of the scraper arm comprises a portion in which a length of the flat paddle blade portion in an axial direction of the cylindrical container shortens gradually from the rotating shaft toward a direction of a side surface of the cylindrical container.

9. A method for producing methacrylic acid, comprising:
forming raw material methacrylic acid; and
purifying the raw material methacrylic acid by the method according to claim 1.

10. The method for producing methacrylic acid according to claim 9, further comprising:
subjecting, to solid-liquid separation, a suspension slurry formed by the purifying of the raw material methacrylic acid; and
purifying a solid obtained by the solid-liquid separation, by a high purity operation.

11. The method for producing methacrylic acid according to claim 1, wherein the purity of the raw material methacrylic acid is in a range of 99.00 to 99.99% by mass.

12. The method for producing methacrylic acid according to claim 1, wherein the purity of the raw material methacrylic acid is in a range of 99.00 to 99.90% by mass.

13. The method for producing methacrylic acid according to claim 1, wherein the raw material methacrylic acid and methanol are mixed so that a concentration of methanol in the mixed solution is 3.1 to 3.75% by mass.

14. The method for producing methacrylic acid according to claim 1, further comprising conducting a high purity operation for removing the remaining mother liquor including methanol from the crystal.

* * * * *